(12) United States Patent
Jung et al.

(10) Patent No.: US 8,164,075 B2
(45) Date of Patent: Apr. 24, 2012

(54) TREATMENT APPARATUSES AND METHODS USING PROTON

(75) Inventors: Moon Youn Jung, Daejeon (KR); Nam Soo Myung, Seongnam (KR); Hyun Woo Song, Daejeon (KR); Hyeon-Bong Pyo, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 132 days.

(21) Appl. No.: 12/836,489

(22) Filed: Jul. 14, 2010

(65) Prior Publication Data
US 2011/0147619 A1    Jun. 23, 2011

(30) Foreign Application Priority Data
Dec. 18, 2009   (KR) .......................... 10-2009-0127223

(51) Int. Cl.
*A61N 5/00* (2006.01)
*H01J 3/00* (2006.01)

(52) U.S. Cl. .................... 250/492.3; 250/505.1; 600/411
(58) Field of Classification Search ............... 250/492.1, 250/492.3, 505.1, 526; 378/64, 65; 600/407, 600/411; 324/309
See application file for complete search history.

(56) References Cited

U.S. PATENT DOCUMENTS

| | | | |
|---|---|---|---|
| 5,440,133 A * | 8/1995 | Moyers et al. ............. | 250/492.3 |
| 7,640,052 B2 * | 12/2009 | Weinstock .................... | 600/407 |
| 7,728,311 B2 * | 6/2010 | Gall ........................ | 250/492.21 |
| 8,089,054 B2 * | 1/2012 | Balakin ....................... | 250/492.1 |
| 2010/0142678 A1 * | 6/2010 | Myung et al. ................... | 378/65 |
| 2011/0218420 A1 * | 9/2011 | Carlone et al. ................ | 600/411 |

* cited by examiner

*Primary Examiner* — Bernard E Souw

(57) ABSTRACT

A treatment apparatus using proton includes a proton generation unit and a magnet. The proton generation unit projects proton into a tumor site of a patient, and the magnet forms a magnetic field around the patient. The proton conducts a spiral motion due to collision with atom of the tumor site and Lorenz force generated by the magnetic field.

13 Claims, 2 Drawing Sheets

TREATMENT APPARATUSES AND METHODS USING PROTON

CROSS-REFERENCE TO RELATED APPLICATIONS

This U.S. non-provisional patent application claims priority under 35 U.S.C. §119 of Korean Patent Application No. 10-2009-0127223, filed on Dec. 18, 2009, the entire contents of which are hereby incorporated by reference.

BACKGROUND OF THE INVENTION

The present invention disclosed herein relates to treatment apparatuses and methods, and more particularly, to treatment apparatuses and methods using proton.

Due to much stress and irregular meal, modern people living in complex society have difficulty in maintaining their health. In particular, such modern people have the highest malignant tumor (i.e., cancer) death rate. The cancer occurrence rate also tends to increase, and, national countermeasure is urgently demanded.

Effective cancer treatments may be most easily achieved by the early detection of malignant tumors. Most cancer treatment technologies, except for chemical therapy, are performed on exact tumor sites within organs, e.g., brain, breast, ovary, large intestine.

When abnormal cell masses are combined to a sufficient size, target recognition and local concentration become easy. Therefore, tumor masses may be removed by surgery operations, or may be destroyed by heating, cooling, radiation, or chemical therapy. However, cancers are metastasized and spread from the original site to adjacent organs by diffusion of abnormal cells. Consequently, there is a need for methods which can effectively and selectively treat tumor masses.

SUMMARY OF THE INVENTION

The present invention provides a treatment apparatus using proton, which has an improved treatment effect on tumor sites.

The present invention also provides a treatment method using proton, which has an improved treatment effect on tumor sites.

Embodiments of the present invention provide treatment apparatuses using proton, including: a proton generation unit projecting proton into a tumor site of a patient; and a magnet forming a magnetic field around the patient, wherein the proton conducts a spiral motion due to collision with atom of the tumor site and Lorenz force generated by the magnetic field.

In some embodiments, the spiral motion of the proton may have a stop position within the tumor site.

In other embodiments, the treatment apparatus may further include a bore member having a hollow portion at which the patient is placed, the bore member being disposed inside the magnet.

In still other embodiments, the magnet may include a circular magnet, or a plurality of magnets arranged in a circle.

In even other embodiments, the proton may agitate DNA's double helix or metabolism of a tumor cell of the tumor site.

In yet other embodiments, the proton generation unit may include a laser or an accelerator.

In further embodiments, the accelerator may include a synchrotron accelerator or a cyclotron accelerator.

In still further embodiments, the proton may be projected in a perpendicular or inclined direction with respect to the magnetic field.

In other embodiments of the present invention, treatment methods using proton include: forming a magnetic field surrounding a patient; and projecting proton into a tumor site of the patient, wherein the proton conducts a spiral motion due to collision with atom of the tumor site and Lorenz force generated by the magnetic field.

In some embodiments, the spiral motion of the proton may have a stop position within the tumor site.

In other embodiments, the proton may agitate DNA's double helix or metabolism of a tumor cell of the tumor site.

In still other embodiments, the proton may be projected in a perpendicular or inclined direction with respect to the magnetic field.

In even other embodiments, the treatment method may further include labeling nano-particles in the tumor site.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DETAILED DESCRIPTION OF PREFERRED EMBODIMENTS

Figure 1:
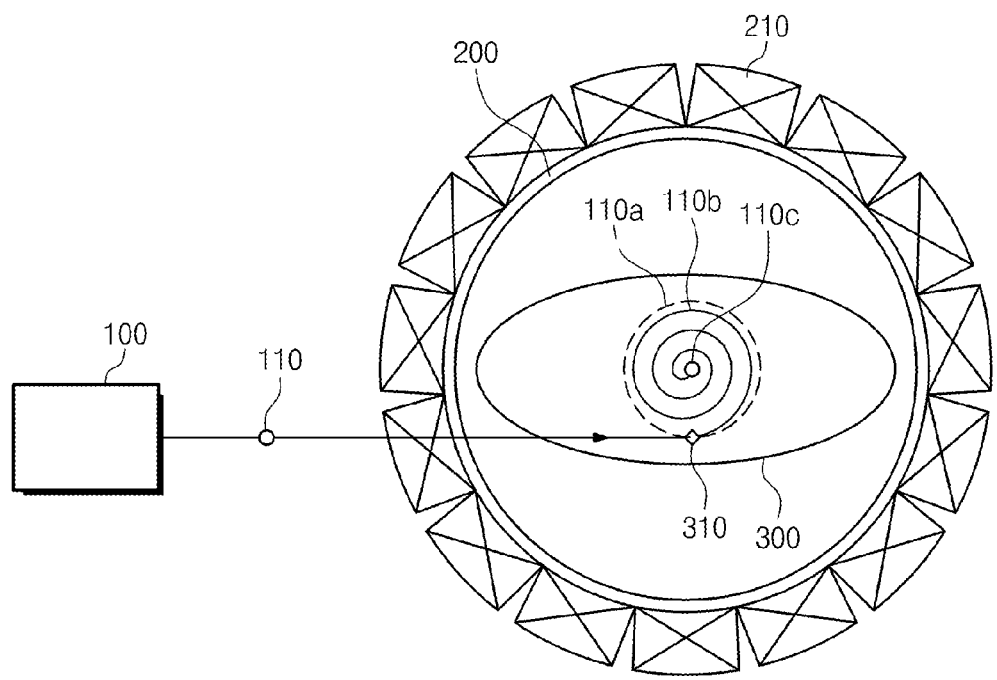
FIG. 1 is a sectional view illustrating the schematic configuration of a treatment apparatus using proton according to an embodiment of the present invention.

Preferred embodiments of the present invention will be described below in more detail with reference to the accompanying drawings. Advantages and features of the present invention, and implementation methods thereof will be clarified through following embodiments described with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Further, the present invention is only defined by scopes of claims. Like reference numerals refer to like elements throughout.

In the following description, the technical terms are used only for explain a specific exemplary embodiment while not limiting the present invention. The terms of a singular form may include plural forms unless referred to the contrary. The meaning of "include," "comprise," "including," or "comprising," specifies a property, a region, a fixed number, a step, a process, an element and/or a component but does not exclude other properties, regions, fixed numbers, steps, processes, elements and/or components. Since preferred embodiments are provided below, the order of the reference numerals given in the description is not limited thereto.

Additionally, the embodiment in the detailed description will be described with sectional views as ideal exemplary views of the present invention. In the figures, the dimensions of layers and regions are exaggerated for clarity of illustration. Accordingly, shapes of the exemplary views may be modified according to manufacturing techniques and/or allowable errors. Therefore, the embodiments of the present invention are not limited to the specific shape illustrated in the exemplary views, but may include other shapes that may be created according to manufacturing processes. Areas exemplified in the drawings have general properties, and are used to illustrate a specific shape of a semiconductor package region. Thus, this should not be construed as limited to the scope of the present invention.

First, the Lorenz force will be described below.

In physics, the Lorenz force is a force on a charged particle due to the electromagnetic field. The charged particle experiences an electric field force when placed in the electric field, and experiences a magnetic field force when moved within the magnetic field. The Lorenz force equation is a combination of the two forces.

$$F = q(E + v \times B) \quad (1)$$

where,

F: Lorenz force
E: Electric field
B: Magnetic field
q: Charge of particle
v: Velocity of particle Referring to Equation (1) above, a positively charged particle is accelerated within the electric field, and moves in a circle at a constant velocity according to the right-hand rule because of the outer product when passing through the magnetic field. Hendrik Antoon Lorenz introduced this force, so this force is called Lorenz force.

FIG. 1 is a sectional view illustrating the schematic configuration of a treatment apparatus using proton according to an embodiment of the present invention.

Referring to FIG. 1, the treatment apparatus using proton includes a proton generation unit 100 and a magnet 210.

Figure 2:
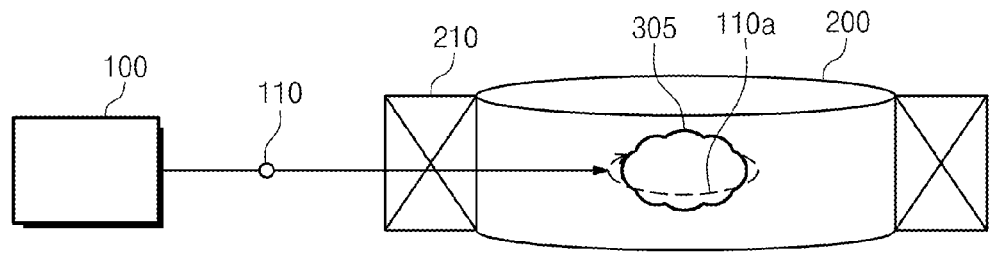
FIGS. 2 and 3 are schematic conceptual diagrams illustrating motion types of the proton in the treatment apparatus using proton according to the embodiment of the present invention.
Figure 3:
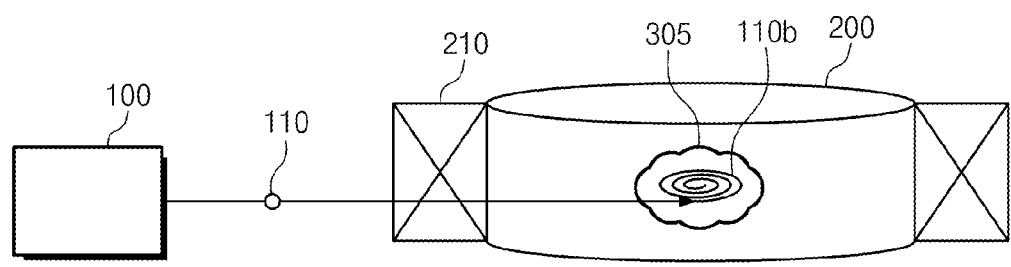
Figure 4:
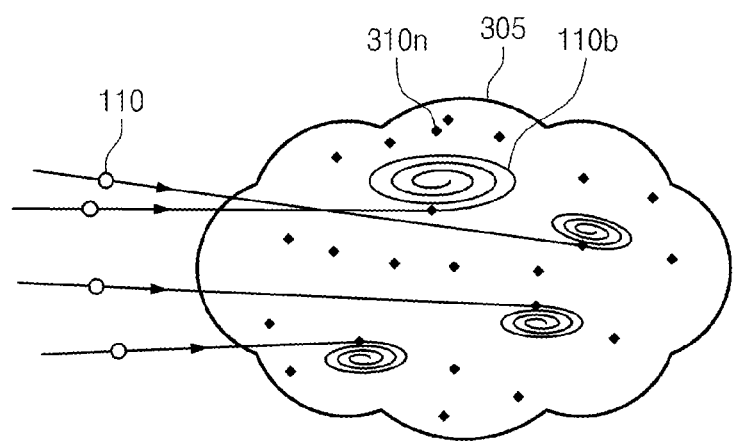
FIG. 4 is a schematic conceptual diagram illustrating a method of improving a treatment effect in a treatment apparatus using proton according to an embodiment of the present invention.

The proton generation unit 100 may project proton 110 into a tumor site of a patient 300 (see 305 in FIGS. 2 to 4). The proton generation unit 100 may be a high power laser or a proton accelerator. If the high power laser is included in the proton generation unit 100, the proton generation unit 100 may further include target material generating the proton 110 by high power laser pulses. The proton accelerator may be a synchrotron accelerator or a cyclotron accelerator. Accordingly, the proton 110 may be a high energy proton.

The magnet 210 may form a magnetic field surrounding the patient 300. The magnet 210 may include a circular magnet or a plurality of magnets arranged in a circle. The magnet 210 may include an electromagnet.

The treatment apparatus using proton may have a hollow portion at which the patient 300 is placed, and may further include a bore member 200. The magnet 210 may be disposed outside the bore member 200. The inside of the bore member 200 may be in a vacuum state.

The proton 110 may be set to and projected into a position of the tumor site obtained from imaging diagnosis equipment, e.g., a magnetic resonance imaging (MRI), a computer tomography (CT), a positron emission tomography (PET), or an ultrasonic wave device, which is used for diagnosis of the tumor site of the patient 300.

According to the treatment principle of the treatment apparatus using proton, when the patient 300 enters the inside of the bore member 200, the magnetic field formed by the magnet 210 surrounds the patient 300, and the proton 110 generated from the proton generation unit 100 is projected from the outside of the magnet 210 into the body of the patient 300. The proton 110 projected into the body of the patient 300 collides with an atom 310 of the tumor site existing inside the body of the patient 300. The proton 110 which loses its energy by the collision conducts a spiral motion 110b due to the Lorenz force which is generated by the magnetic field formed by the magnet 210. The proton 110 conducting the spiral motion 110b agitates tumor cells of the tumor site, and the proton 110 gradually loses its energy while agitating the tumor cells of the tumor site. Finally, the proton 110 completely loses its energy and reaches a stop position 110c where the velocity of the proton 110 is zero.

That is, the proton 110 agitates the tumor cells of the tumor site by the collision with the atom 310 of the tumor site and the spiral motion 110b conducted by the Lorenz force which is generated by the magnetic field formed by the magnet 210. In this way, the proton 110 may inhibit the growth of the tumor cells or destroy the tumor cells. The proton 110 may agitate DNA's double helix of the tumor cell, or agitate metabolism within nuclear of the tumor cell.

The spiral motion 110b of the proton 110 may increase the probability that will agitate the tumor cells of the tumor site. Furthermore, the stop position 110c of the spiral motion 110b of the proton 110 may be located at the tumor site. Accordingly, the treatment effect of the treatment apparatus using proton may be improved.

On the other hand, if the proton 110 projected into the body of the patient 300 does not collide with the atom 310 of the tumor site existing inside the body of the patient 300, the proton 110 which does not lose its energy conducts a simple uniform circular motion 110a by the Lorenz force generated by the magnetic field formed by the magnet 210, as indicated by dotted lines.

A typical treatment apparatus using proton projects proton into the tumor site, while not placing the patient within the magnetic field. When the proton collides with the atom of the tumor site in a space where no magnetic field is present, the proton is bounded in a nonspecific direction or stopped. However, in the case of the treatment apparatus according to the embodiment of the present invention, the patient is placed within the magnetic field. The proton which loses a part of the initial projection energy due to the collision with the atom of the tumor site conducts the spiral motion due to the Lorenz force generated by the magnetic field, thereby increasing the probability which will agitate the tumor cells of the tumor site.

Compared with the space where no magnetic field is present, the proton conducting the spiral motion in the space surrounded by the magnetic field further agitates the tumor cells of the tumor site.

FIGS. 2 and 3 are schematic conceptual diagrams illustrating motion types of the proton in the treatment apparatus using proton according to the embodiment of the present invention.

Referring to FIG. 2, if the proton 110 generated from the proton generation unit 100 is projected into the bore member 200, which is in the vacuum state, and does not collide with the tumor site 305, the proton 110 does not lose its initial projection energy. The proton 110 which does not lose its initial projection energy conducts the simple uniform circular motion 110a around the tumor site 305 by the Lorenz force generated by the magnetic field formed by the magnet 210, as indicated by dotted lines.

Since the Lorenz force is given as Equation (1) above, the proton 110 projected in a direction perpendicular to the magnetic field continuously conducts the circular motion 110a within the bore member 202, while maintaining an initial projection velocity within the magnetic field.

Referring to FIG. 3, if the proton 110 generated from the proton generation unit 100 is projected into the bore member 200, which is in the vacuum state, and collides with the atom (see 310 in FIG. 1) of the tumor site 305, the proton 110 loses a portion of its initial projection energy due to the collision with the atom of the tumor site 305. The proton 110 which loses a part of its initial projection energy conducts the spiral motion 110b due to the Lorenz force generated by the magnetic field formed by the magnet 210. The proton 110 conducting the spiral motion 110b gradually loses its energy while agitating the tumor cells of the tumor site 305. Finally, the proton 110 completely loses its energy and reaches the stop position (see 110c in FIG. 1) within the tumor site 305.

FIG. 3 illustrates a case where the proton 110 is projected in a direction perpendicular to the magnetic field. Although not shown, if the proton 110 is projected in an inclined direction with respect to the magnetic field, the proton 110 may conduct the spiral motion 110b after the collision with the atom of the tumor site 305 and also conduct a motion in an axial direction of the magnetic field. The proton 110 which continuously agitates the tumor cells of the tumor site 305 while conducting the spiral motion 110b and the motion in the axial direction of the magnetic field gradually loses its energy and stops at a specific position.

FIG. 4 is a schematic conceptual diagram illustrating a method of improving a treatment effect in a treatment apparatus using proton according to an embodiment of the present invention.

Referring to FIG. 4, nano-particles 310n may be labeled in the tumor site 305 to be treated by the treatment apparatus using proton. The nano-particles 310n may increase the probability of collision between the proton 110 and the tumor site 305.

As illustrated in FIG. 4, the protons 110 projected into the tumor site 305 may agitate the tumor cells of the tumor site 305 while conducting the spiral motion 110b due to the collision with the nano-particles 310n labeled in the tumor site 305. The protons 110 conducting the spiral motion 110b may increase the probability that inhibits the growth of the tumor cells of the tumor site 305, or destroys the tumor cells of the tumor site 305.

In addition, the nano-particles 110n labeled in the tumor site 305 may make a difference in the probability of collision between the protons 110 and the normal cells and the probability of collision between the protons 110 and the tumor cells. Accordingly, it is possible to implement a method which is capable of inhibiting the growth of the tumor cells of the tumor site 305 or destroy the tumor cells of the tumor site 305 more intensively.

In the treatment apparatus using proton according to the embodiment of the present invention, the protons experience the Lorenz force generated by the magnetic field and thus conduct the spiral motion within the tumor site, thereby increasing the probability which agitate the tumor cells of the tumor site. Therefore, the tumor site may be treated more effectively.

In addition, in the treatment method using proton according to the embodiment of the present invention, the tumor site includes the nano-particles, thereby increasing the probability of collision between the proton and the tumor site. Therefore, the tumor site may be treated more effectively.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A treatment apparatus using proton, comprising:
   a proton generation unit projecting proton into a tumor site of a patient; and
   a magnet forming a magnetic field around the patient,
   wherein the proton conducts a spiral motion due to collision with atom of the tumor site and Lorenz force generated by the magnetic field.

2. The treatment apparatus of claim 1, wherein the spiral motion of the proton has a stop position within the tumor site.

3. The treatment apparatus of claim 1, further comprising a bore member having a hollow portion at which the patient is placed, the bore member being disposed inside the magnet.

4. The treatment apparatus of claim 1, wherein the magnet comprises a circular magnet, or a plurality of magnets arranged in a circle.

5. The treatment apparatus of claim 1, wherein the proton agitates DNA's double helix or metabolism of a tumor cell of the tumor site.

6. The treatment apparatus of claim 1, wherein the proton generation unit comprises a laser or an accelerator.

7. The treatment apparatus of claim 6, wherein the accelerator comprises a synchrotron accelerator or a cyclotron accelerator.

8. The treatment apparatus of claim 1, wherein the proton is projected in a perpendicular or inclined direction with respect to the magnetic field.

9. A treatment method using proton, comprising:
   forming a magnetic field surrounding a patient; and
   projecting proton into a tumor site of the patient,
   wherein the proton conducts a spiral motion due to collision with atom of the tumor site and Lorenz force generated by the magnetic field.

10. The treatment method of claim 9, wherein the spiral motion of the proton has a stop position within the tumor site.

11. The treatment method of claim 9, wherein the proton agitates DNA's double helix or metabolism of a tumor cell of the tumor site.

12. The treatment method of claim 9, wherein the proton is projected in a perpendicular or inclined direction with respect to the magnetic field.

13. The treatment method of claim 9, further comprising labeling nano-particles in the tumor site.

* * * * *